United States Patent [19]

Levasseur

[11] Patent Number: 5,178,186
[45] Date of Patent: Jan. 12, 1993

[54] AXIAL TWO-WAY VALVE-STOPCOCK COMBINATION

[76] Inventor: Joseph E. Levasseur, Rte. 1, Box 2330, Rockville, Va. 23146

[21] Appl. No.: 669,624

[22] Filed: Mar. 14, 1991

[51] Int. Cl.⁵ .................. F16K 37/00; F16K 5/04; F16K 31/00
[52] U.S. Cl. ................. 137/556; 251/310; 251/345; 251/352
[58] Field of Search ............. 137/556, 556.3, 556.6; 251/310, 344, 345, 352, 904; 604/32, 248

[56] References Cited

U.S. PATENT DOCUMENTS

| | | | |
|---|---|---|---|
| 812,627 | 2/1906 | Wirth et al. | 251/352 X |
| 1,296,239 | 3/1919 | Van Meter | 251/352 X |
| 2,711,846 | 6/1955 | Birchall, Jr. et al. | 251/310 X |
| 3,186,437 | 6/1965 | Buono | 137/625.42 |
| 3,277,922 | 10/1966 | Eisel | 251/345 X |
| 3,472,486 | 10/1969 | Hastings | 251/345 |
| 4,180,068 | 12/1979 | Jacobsen et al. | 128/214 R |
| 4,183,499 | 1/1980 | Swartz et al. | 251/352 X |
| 4,280,498 | 7/1981 | Jensen | 251/352 X |
| 4,397,442 | 8/1983 | Larkin | 251/342 |
| 4,408,631 | 10/1983 | Uhlig et al. | 251/352 X |
| 4,471,942 | 9/1984 | Kocanowski | 251/205 |
| 4,543,990 | 10/1985 | Meuleman | 137/556 |
| 4,560,375 | 12/1985 | Schulte et al. | 604/9 |
| 4,603,837 | 8/1986 | Steer | 251/352 X |
| 4,745,950 | 5/1988 | Mathieu | 137/798 |
| 4,819,684 | 4/1989 | Zaugg et al. | 137/112 |
| 4,850,955 | 7/1989 | Newkirk | 604/9 |
| 4,967,797 | 11/1990 | Manska | 137/625.47 |
| 5,045,068 | 9/1991 | Kawai et al. | 251/352 X |

Primary Examiner—John Rivell
Attorney, Agent, or Firm—Kenyon & Kenyon

[57] ABSTRACT

A valve stem and body combination for flow control in fluid delivery systems for biomedical applications. The valve body includes a smaller conduit that can be aligned with an exit port in the valve stem to achieve a flow-through mode of operation. The flow through the stopcock is controlled by axially turning the valve stem within the valve body, thus making the stopcock streamline in operation. A dead stop combination is provided for assuring an open and closed state of the stopcock. In addition, the valve stem and body can be marked to assist the user in aligning the exit port and smaller conduit.

18 Claims, 6 Drawing Sheets

AXIAL TWO-WAY VALVE-STOPCOCK COMBINATION

BACKGROUND OF THE INVENTION

The present invention relates to fluid delivery systems for biomedical applications, and, more particularly, to a valve-stopcock combination having a rotatable valve stem oriented in the same axis as the flow.

A large variety of fluid delivery systems exist for biomedical applications in the hospital and research laboratory environments. Directional flow in these systems is controlled by valves which are conventionally referred to as stopcocks. These stopcocks come in two-way, three-way, and four-way configurations. The stems in these configurations are usually oriented perpendicular to the axis of fluid flow.

Typical perpendicular orientation is described in U.S. Pat. Nos. 3,186,437 and 4,819,684. Bored extended portions are coupled to a stopcock at a 90° angle. By turning an actuator, the extended portion lines up with a perpendicular groove in the stopcock.

In U.S. Pat. No. 4,180,068, a bi-directional catheter is described. This catheter includes a primary tube and a pair of branching tubes oriented at 45° angles.

In U.S. Pat. No. 4,397,442, an in-line sleeve valve is described. This valve allows a streamline flow by removal of a sealing plug from the valve opening. The flow is stopped by manually pushing the sealing plug back into the tubular sleeve.

In U.S. Pat. No. 4,471,942, an in-line valve is shown having a valve controller disk. Turning of this disk controls the longitudinal displacement of a gate member which obstructs the valve flow.

In U.S. Pat. Nos. 4,560,375 and 4,850,955 another valve control is described that can be surgically implanted. Although in-line, this valve operates by changing the thickness of a resilient membrane as opposed to mechanical operation.

U.S. Pat. No. 4,745,950 describes a valve connector that operates through a spring activated plate in the flow-path. The plate controls the valve operation in dependence on the pressure within the connector.

U.S. Pat. No. 4,967,797 describes a tap valve. A rotating actuator includes a channel which allows fluid communication between a throughput tube and tapping ports oriented at 45° angles.

The aforementioned valves do not offer a streamline profile. Therefore, these systems can not be used in several physically restrictive applications. There is also a need for a stopcock-valve combination that is simple and economic in design and manufacture.

SUMMARY OF THE INVENTION

These and other needs are satisfied by the valve-stopcock combination of the present invention. The axial stopcock includes a valve body having a bored base having an opening. This opening receives an element of a fluid delivery system. The valve body has a main section coupled to the bored base. This main section includes a bored conduit extending completely through the main section and coupled to the opening of the bored base. The main section also includes a smaller conduit coupled laterally to the bored conduit and coupled to the opening of the bored base.

The stopcock includes a valve stem which includes a main body and a distal section coupled to the main body. The distal section has a cylindrical surface which includes a surface opening. The valve stem also includes an axial conduit extending completely through the main body and having a first end and a distal end. The axial conduit extends partially through the distal section, such that the distal end is within the distal section. An exit port is coupled perpendicularly to the distal end of the axial conduit and is coupled to the opening in the distal section. When the distal section is inserted into the bored conduit of the valve body, the exit port is aligned with the smaller conduit of the valve body.

A thin-walled extension is coupled to the main section of the valve body. This extension comprises two arcuate sections of a thin-walled cylinder, each of which includes a concave circular groove. A convex circular flange is coupled to the main body of the valve stem, such that the flange fits into the circular groove and secures the valve stem to the valve body.

The main section of the valve body includes a recessed groove which has an arcuate shape and is coupled circumferentially to the bored conduit of the valve body. The main body of the valve stem includes an extension which fits into the recessed groove when the valve body is coupled to the valve stem. The extension and the recessed groove limit axial rotation of the valve stem with respect to the valve body.

A knurled wheel is coupled circumferentially to the main body of the valve stem, such that manual rotation of the knurled wheel causes the valve stem to rotate. The main body of the valve stem also includes a Luer lock end which opens and closes the stopcock.

A surface recess is provided within the main section of the valve body which is circumferentially aligned with the smaller conduit of the valve body. Also, a bar is provided which is coupled to the main body of the valve stem and is circumferentially aligned with the exit port and opening of the distal section of the valve stem. The surface recess and bar can be colored, and they facilitate alignment of the exit port of the valve stem with the smaller conduit of the valve body. Also the knurl of the knurled wheel which is circumferentially aligned with the exit port of the valve stem can be colored.

The above is a brief description of some deficiencies in disclosed valve devices and advantages of the present invention. Other features, advantages and embodiments of the invention will be apparent to those skilled in the art from the following description, accompanying drawings and appended claims.

DETAILED DESCRIPTION

Figure 1A:
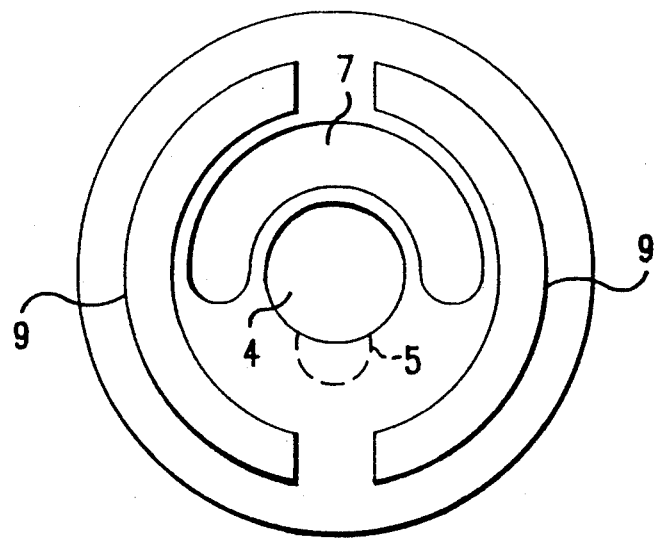
FIG. 1 is a schematic diagram of the valve body of the present invention.
Figure 1B:
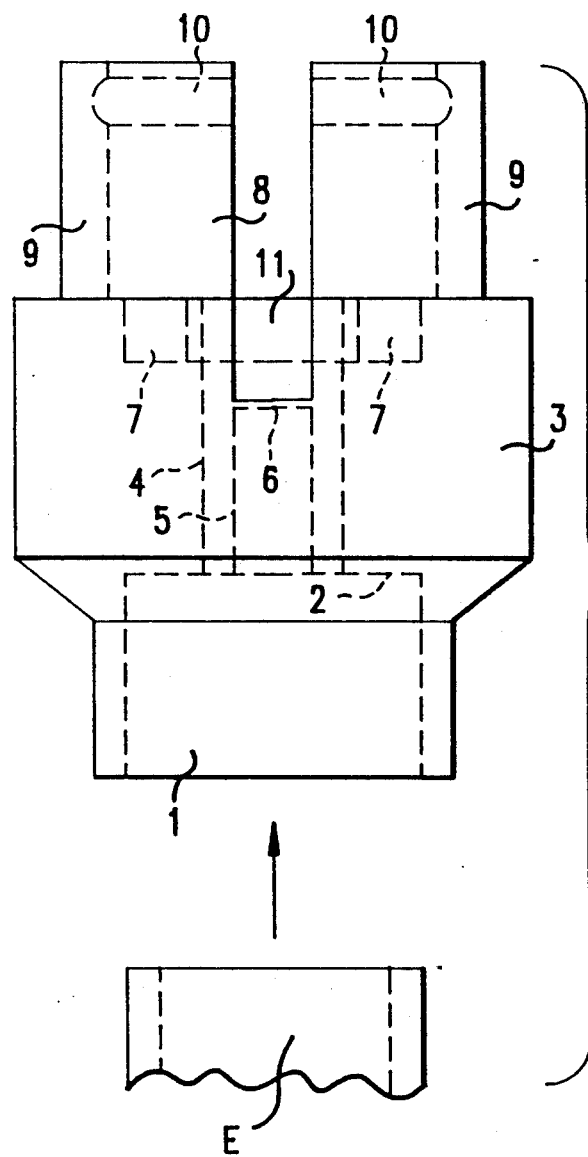

Referring to FIG. 1, the valve body of the present invention is shown. The valve body includes a bored base 1 for receiving a desired element E of a fluid delivery system. The base 1 is press-fitted onto the element E, such that the element E is positioned at a stop 2 in the base 1. The element E is fused to the valve body with any of a variety of plastic solvents well known in the art. The standard male connector known to those skilled in the art in stopcocks can be substituted for the base 1.

Figure 2:
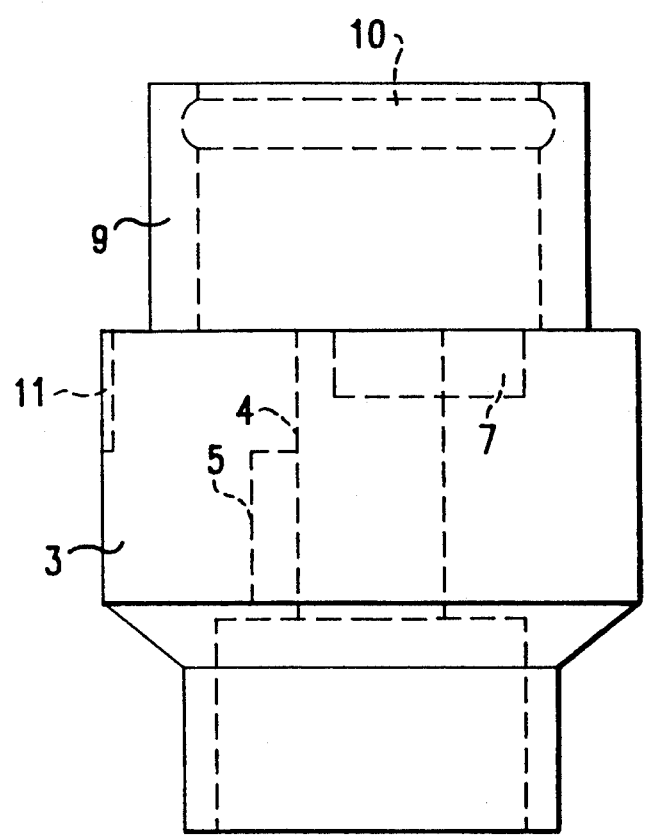
FIG. 2 is a schematic diagram of the valve body of FIG. 1 rotate 90°.

A main section 3 is disposed above the base 1. The main section 3 includes a bored conduit 4 which extends completely through the main section 3 to the opening in the base 1. The diameter of the bored conduit 4 serves as a standard for all other dimensions in the stopcock. A smaller conduit 5, having a diameter half that of the bored conduit 4, extends from the opening in the base 1 to a stop 6 in the main section 3 The stop 6 is placed a distance equal to one-quarter the diameter of the bored conduit 4 above the longitudinal midpoint of the main section 3. The center line of the smaller conduit 5 lies on the radial edge of the bored conduit 4, which gives the cross-sectional view of the smaller conduit 5 a half-moon appearance. The location of the smaller conduit 5 in relation to the bored conduit 4 is clearly shown in FIG. 2, which depicts the valve body of FIG. 1 rotated 90°.

A recessed groove 7 is routed into the upper side of the main section 3. This recessed groove 7 extends 180° on the side contralateral to the smaller conduit 5 with a depth equal to one-half the diameter of the bored conduit 4. The diameter of the recessed groove 7 is also one-half the diameter of the bored conduit 4. An upper section 8 is coupled to the upper side of the main section 3. This upper section 8 includes a thin-walled extension 9 which resembles a bisected cylindrical shell. This bisection has a width equal to one-half the diameter of the bored conduit 4 and extends through the center of the smaller conduit 5 and at a 90° rotation to the recessed groove 7 (as viewed from the upper surface of the main section 3). The thin-walled extension 9 includes a concave circular groove 10 having a depth equal to one-quarter the diameter of the bored conduit 4. The concave circular groove 10 is located near the upper edge of the thin-walled extension 9 and serves as part of a retainer mechanism for securing a valve stem to the valve body as described with reference to FIG. 3. A surface recess 11 is included in the main section 3 to assist in locating the smaller conduit 5 with respect to the circumference of the valve body. This surface recess can be colored to assist the user when handling the valve body.

Figure 3A:
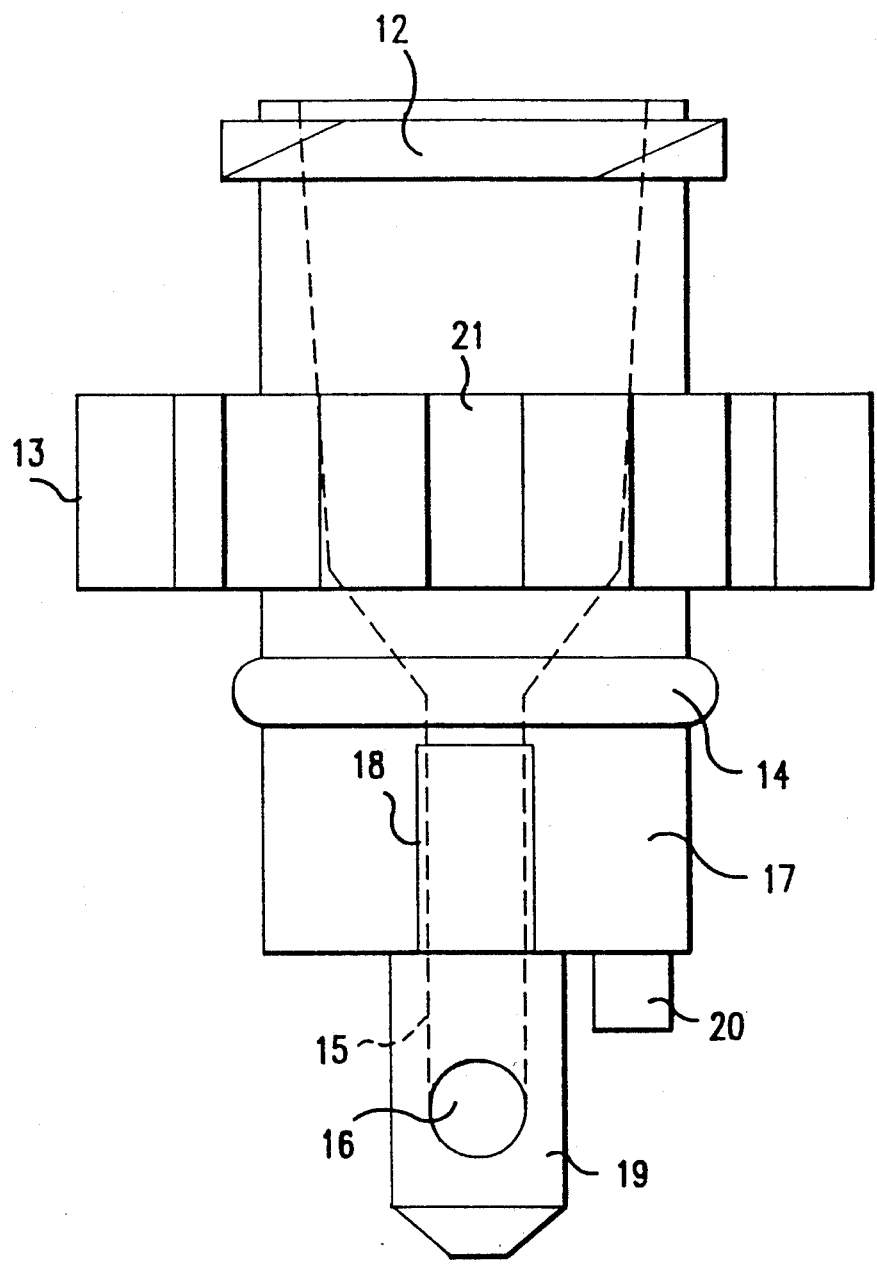
FIG. 3 is a schematic diagram of the valve stem of the present invention.
Figure 3B:
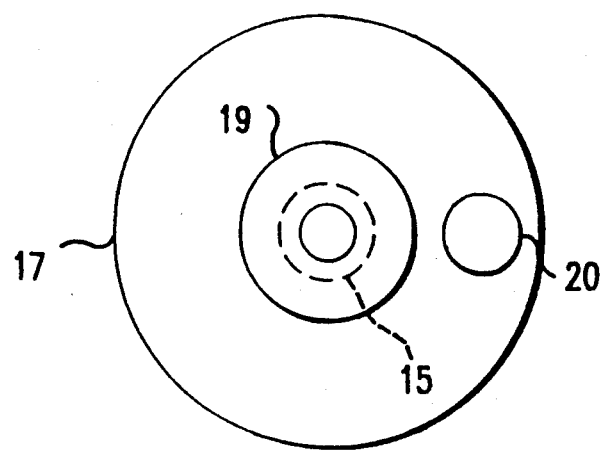

Referring to FIG. 3, the valve stem of the present invention is shown. This valve stem serves the combined functions of opening and closing the valve as well as being the adaptive female component of the stopcock. The valve stem includes a standard Luer lock end 12 coupled to a main body 17. A knurled wheel 13 coupled around the main body 17 facilitates the manual turning of the valve stem. The main body also includes a convex circular flange 14 having a radius approximately equal to the radius of the concave circular groove 10. Mating of the convex circular flange 14 and concave circular groove 10 effectively interlocks the valve stem into the valve body. A distal section 19 is coupled to the lower surface of the main body 17. The distal section 19 includes an exit port 16. The main body 17 includes an axial conduit 15 which extends from the upper surface of the valve stem to the exit port 16. The axial conduit 15 tapers off somewhat from a large area proximately to the lock end 12 to the diameter of the smaller conduit 5 (FIG. 1) at the exit port 16.

A color-coated bar 18 is externally impressed onto the main body 17 and is aligned with the exit port 16. The color-coated bar 18 allows the user to visually identify the location of the exit port 16 with respect to the circumference of the main body 17 and distal section 19. A color-coated knurl 21 can also be provided on the knurled wheel 13 for the same purpose. After the valve stem is inserted into the valve body, the surface recess 11 of the valve body (FIG. 1) is aligned with the color-coated bar 18 and color-coated knurl 21 of the valve stem in order to align the smaller conduit 5 (FIG. 1) with the exit port 16. This is also known as the flow-through mode of operation. The distal section 19 into the bored conduit 4 (FIG. 1) of the valve body. An extension 20, having a diameter approximately equal to one-half the diameter of the bored conduit 4 (FIG. 1), is coupled to the main body 17 of the valve stem and fits into the recessed groove 7 of the valve body. The extension 20 serves to limit the rotation of the valve body relative to the valve stem to 180°. The extension 20 also serves as a dead stop for fully open and fully closed positions of the valve stem.

Figure 4:
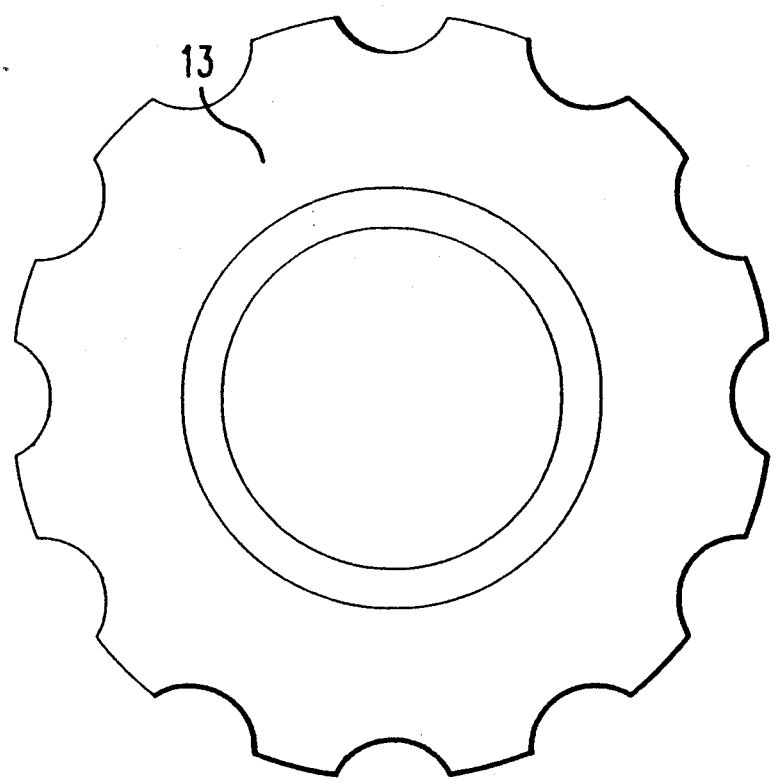
FIG. 4 is a schematic diagram of a cross-section of the valve stem of FIG. 3.

Referring to FIG. 4, a cross sectional view of the knurled wheel 13 is shown. In this example, the knurled wheel 13 includes 12 knurls which allows the user to achieve a firm, non-slip grip when turning the valve stem.

Figure 5:
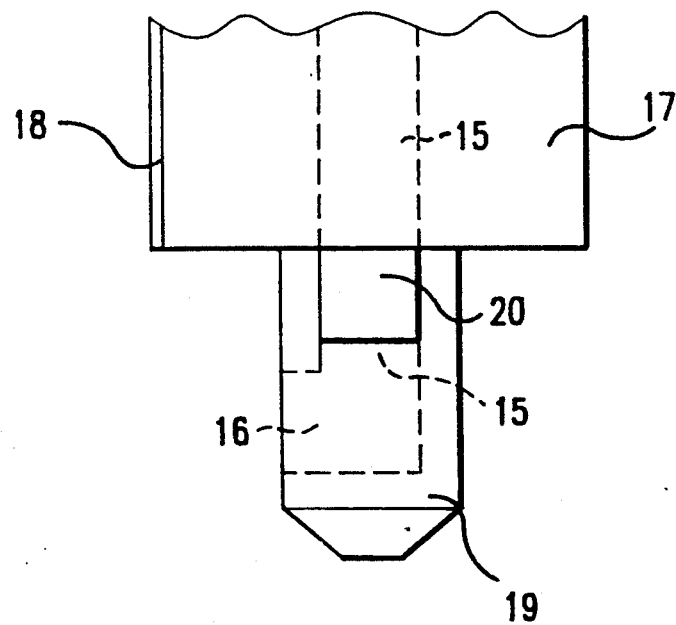
FIG. 5 is a schematic diagram of a cross-section of a segment of the valve stem of FIG. 3 rotated 90°.

Referring to FIG. 5, the lower portion of the valve stem is shown rotated 90°. The location of the exit port 16 in relation to the axial conduit 15 is clearly seen.

Figure 6:
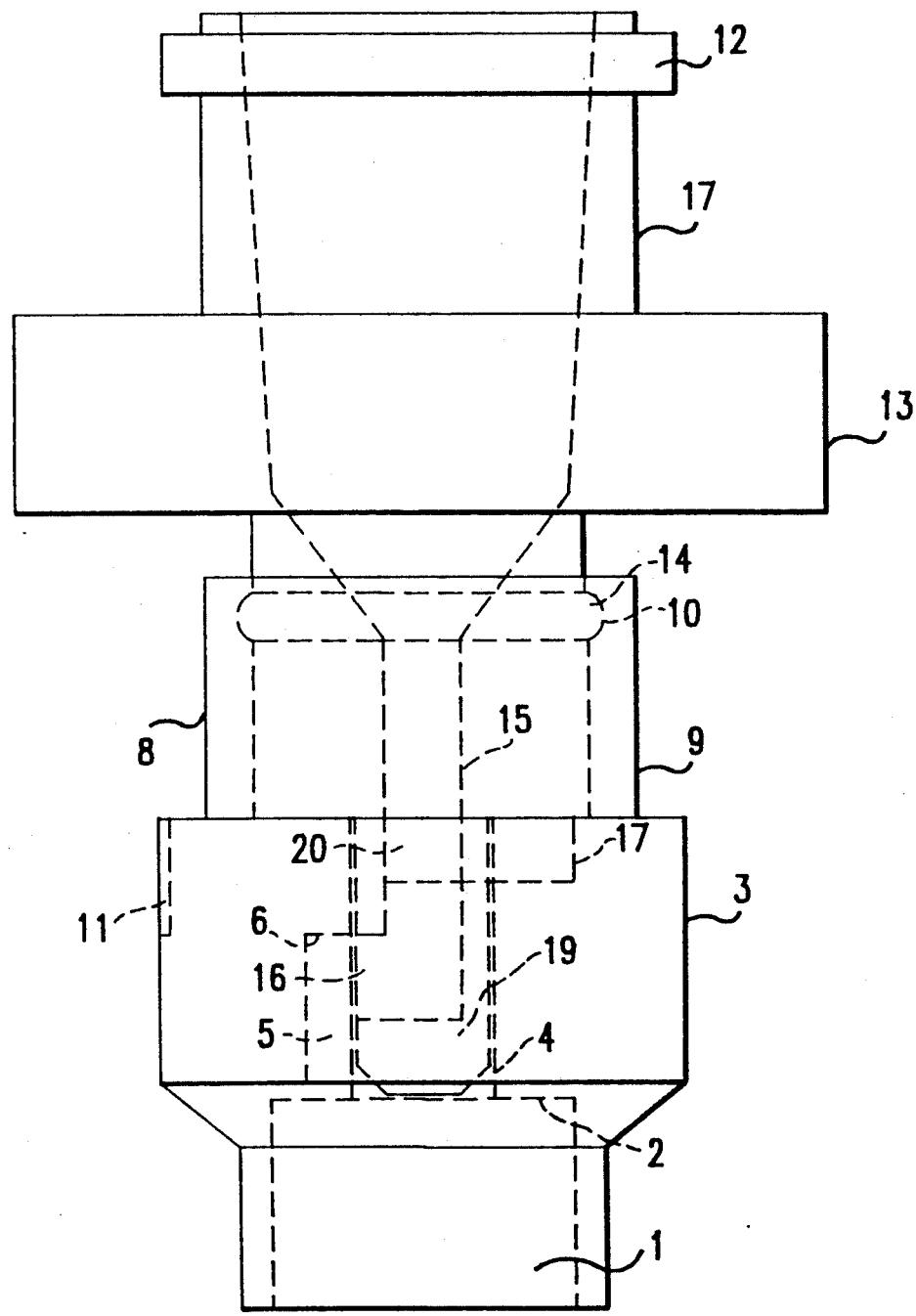
FIG. 6 is a schematic diagram of the assembled stopcock of the present invention in a flow-through position.
Figure 7:
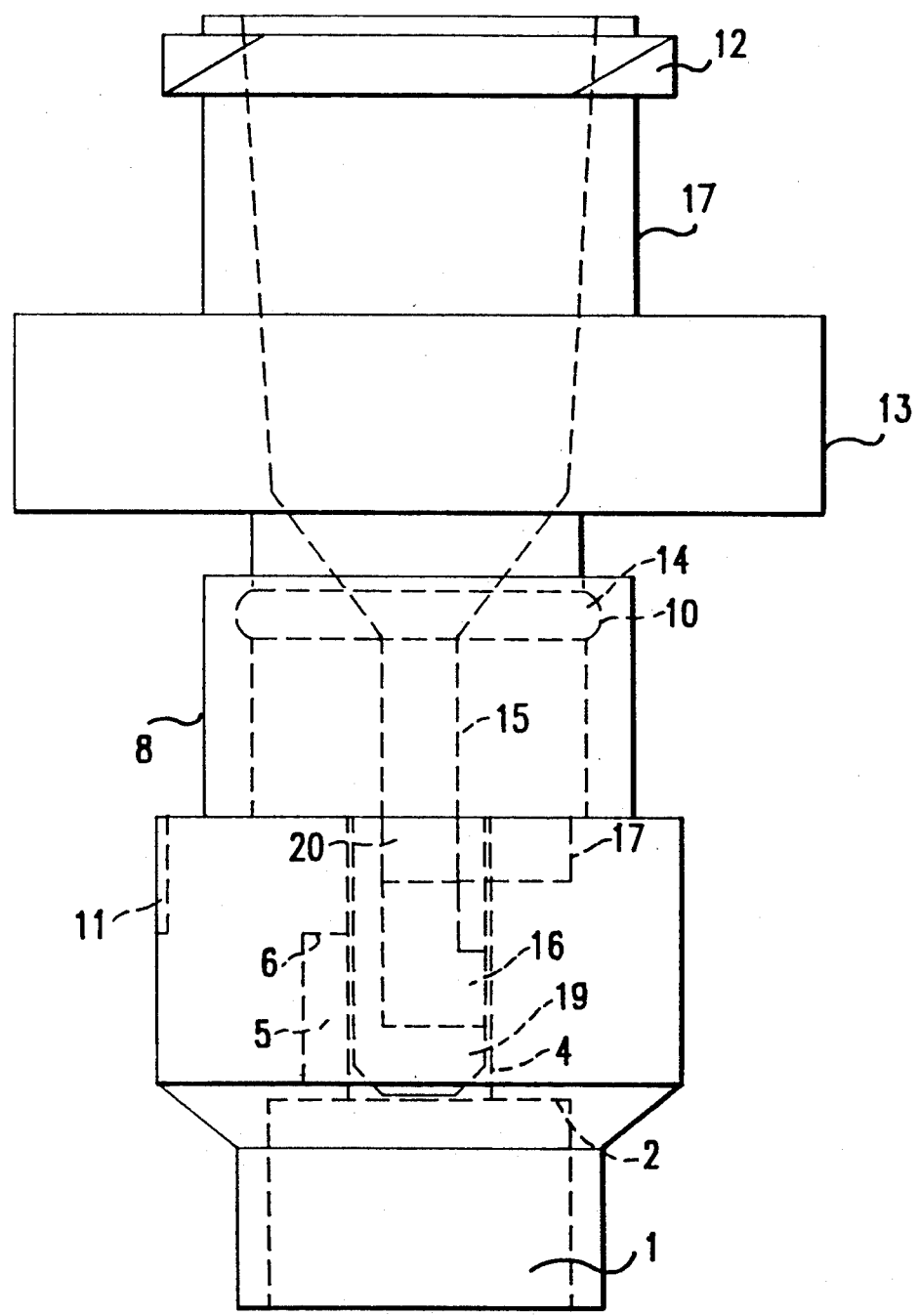
FIG. 7 is a schematic diagram of the stopcock of FIG. 6 in a closed position.

Referring to FIG. 6, the assembled stopcock of the present invention is shown in a flow-through mode of operation. The stopcock is opened or closed by rotating the valve stem within the valve body. The valve stem is turned to a first limit in relation to the valve body due to the extension 20 in the recessed groove 7. In this fully open position the exit port 16 completely lines up with the smaller conduit 5. By rotating the valve stem 180° to a second or opposing limit in relation to the valve body, the stopcock becomes fully closed since exit port 16 is in contralateral alignment with the smaller conduit 5. This fully closed position is shown in FIG. 7. In effect, closure of the stopcock occurs before the valve stem is rotated the entire 180°. Rotation of the valve stem to this second limit does assure the user that the stopcock is closed. During rotation, there is no displacement of the valve stem along the axis of the valve body.

The stopcock is easily assembled by inserting the valve stem into the valve body until the convex flange 14 fits into the convex recess 10 and the extension 20 fits into the recessed groove 7. Because of the convex flange 14, some force is required to snap the valve stem into the valve body. The thin-walled extensions 9 "spring-back" once the flange 14 fits into the recess 10. With proper tolerances, the valve stem and valve body cannot be manually pulled apart.

As a female connector, the valve stem can receive either a non-luer lock syringe or a syringe with a Luer lock. Threading the Luer lock syringe onto the axial stopcock automatically turns the valve stem to its fully open position, thus minimizing handling of the stopcock and possible contamination. By tightly securing a non- Luer lock syringe (e.g., a tuberculin syringe) in the axial stopcock, clockwise rotation of the syringe will also automatically rotate the valve stem to its open position. Before removing the syringe from the stopcock, the valve stem is manually turned counterclockwise to the closed position by grasping the knurled wheel 13 with the fingers. A protective cap (not shown) may be inserted into the female connector of the valve stem to maintain sterility in between use.

The stopcock of the present invention offers a unique streamline valve that is both simple and compact. This stopcock can be used wherever there is a need to access a biomedical fluid delivery system or systems. For example, the stopcock of the present invention can be used to replace the rubber plug on the secondary port of the Abbott Plum cassette, the rubber plugs of intravenous line Y connectors, and intravenous manifolds. In addition, the present form of the valve body, which is shown to have a base 1, may be modified to assume a substitute form as a standard male connector. This would make this two-way valve into a true two-way stopcock.

The above is a detailed description of a particular embodiment of the invention. The full scope of the invention is set out in the claims that follow and their equivalents. Accordingly, the claims and specification should not be construed to unduly narrow the full scope of protection to which the invention is entitled.

What is claimed is:

1. An axial valve-stopcock combination comprising:
    a valve body, comprising:
        a bored base having an opening, said opening receiving an element of a fluid delivery system;
        a main section coupled to said bored base, said main section including a bored conduit extending completely through said main section and coupled to the opening of said bored base, said main section including a smaller conduit coupled laterally to said bored conduit and coupled to the opening of said bored base;
    a valve stem, comprising:
        a main body;
        a distal section coupled to said main body, said distal section having a cylindrical surface and an opening in said cylindrical surface;
        an axial conduit having a first end and a distal end, said axial conduit extending completely through said main body and partially through said distal section, such that said distal end is within said distal section; and
        an exit port coupled perpendicularly to the distal end of said axial conduit, said exit port coupled to the opening in said distal section, whereby when said distal section is inserted into the bored conduit of said valve body, said exit port is capable of being aligned with the smaller conduit of said valve body;
    a thin-walled extension coupled to the main section of said valve body, said extension comprising two arcuate sections of a thin-walled cylinder, each of said sections including a concave circular groove; and
    a convex circular flange coupled to the main body of said valve stem, whereby said flange fits into said circular groove and secures said valve stem to said valve body.

2. The valve-stopcock combination of claim 1, further comprising:
    a recessed groove within the main section of said valve body, said recessed groove having an arcuate shape and coupled circumferentially to the bored conduit of said valve body; and
    an extension coupled to the main body of said valve stem, said extension fitting into said recessed groove when said valve body is coupled to said valve stem, whereby said extension and said recessed groove limit axial rotation of said valve stem with respect to said valve body.

3. The valve-stopcock combination of claim 1, further comprising:
    a knurled wheel coupled circumferentially to the main body of said valve stem, whereby manual rotation of said knurled wheel causes said valve stem to rotate.

4. The valve-stopcock combination of claim 2, further comprising:
    a knurled wheel coupled circumferentially to the main body of said valve stem, whereby manual rotation of said knurled wheel causes said valve stem to rotate.

5. The valve-stopcock combination of claim 2, further comprising:
    a Luer lock end coupled to the main body of said valve stem, said lock end opening and closing said stopcock.

6. The valve-stopcock combination of claim 5, further comprising:
    a Luer lock end coupled to the main body of said valve stem, said lock end opening and closing said stopcock.

7. The valve-stopcock combination of claim 1, further comprising:
    a surface recess within the main section of said valve body, said surface recess circumferentially aligned with the smaller conduit of said valve body; and
    a bar coupled to the main body of said valve stem, said bar circumferentially aligned with the exit port and opening of the distal section of said valve stem, whereby alignment of said surface recess with said bar indicates alignment of the exit port of said valve stem with the smaller conduit of said valve body.

8. The valve-stopcock combination of claim 7, wherein said surface recess and bar are colored.

9. The valve-stopcock combination of claim 6, further comprising:
    a surface recess within the main section of said valve body, said surface recess circumferentially aligned with the smaller conduit of said valve body; and
    a bar coupled to the main body of said valve stem, said bar circumferentially aligned with the exit port and opening of the distal section of said valve stem, whereby alignment of said surface recess with said bar indicates alignment of the exit port of said valve stem with the smaller conduit of said valve body.

10. The valve-stopcock combination of claim 9, wherein said surface recess and bar are colored.

11. The valve-stopcock combination of claim 3, wherein one of the knurls of said knurled wheel is colored, said colored knurl circumferentially aligned with the exit port of said valve stem.

12. The valve-stopcock combination of claim 10, wherein one of the knurls of said knurled wheel is colored, said colored knurl circumferentially aligned with the exit port of said valve stem.

13. The valve-stopcock combination of claim 1, wherein said valve stem is capable of being rotated about said axial conduit to selectively align the exit port of said valve stem with the smaller conduit of said valve body.

14. The valve-stopcock combination of claim 1, wherein said valve stem operates as a female connector at the first end of said axial conduit.

15. The valve-stopcock combination of claim 14, wherein said valve body operates as a male connector at said bored base.

16. An axial valve-stopcock combination comprising:
a valve body, comprising:
   a bored base having an opening, said opening receiving an element of a fluid delivery system;
   a main section coupled to said bored base, said main section including a bored conduit extending completely through said main section and coupled to the opening of said bored base, said main section including a smaller conduit coupled laterally to said bored conduit and coupled to the opening of said bored base;
a valve stem, comprising:
   a main body;
   a distal section coupled to said main body, said distal section having a cylindrical surface and an opening in said cylindrical surface;
   an axial conduit having a first end and a distal end, said axial conduit extending completely through said main body and partially through said distal section, such that said distal end is within said distal section; and
   an exit port coupled perpendicularly to the distal end of said axial conduit, said exit port coupled to the opening in said distal section, whereby when said distal section is inserted into the bored conduit of said valve body, said exit port is capable of being aligned with the smaller conduit of said valve body;
a thin-walled extension coupled to the main section of said valve body, said extension comprising two arcuate sections of a thin-walled cylinder, each of said sections including a concave circular groove;
a convex circular flange coupled to the main body of said valve stem, whereby said flange fits into said circular groove and secures said valve stem to said valve body; and
a Luer lock end coupled to the main body of said valve stem, said lock end opening and closing said stopcock.

17. An axial valve-stopcock combination comprising:
a valve body, comprising:
   a bored base having an opening, said opening receiving an element of a fluid delivery system;
   a main section coupled to said bored base, said main section including a bored conduit extending completely through said main section and coupled to the opening of said bored base, said main section including a smaller conduit coupled laterally to said bored conduit and coupled to the opening of said bored base;
a valve stem, comprising:
   a main body;
   a distal section coupled to said main body, said distal section having a cylindrical surface and an opening in said cylindrical surface;
   an axial conduit having a first end and a distal end, said axial conduit extending completely through said main body and partially through said distal section, such that said distal end is within said distal section; and
   an exit port coupled perpendicularly to the distal end of said axial conduit, said exit port coupled to the opening in said distal section, whereby when said distal section is inserted into the bored conduit of said valve body, said exit port is capable of being aligned with the smaller conduit of said valve body;
a surface recess within the main section of said valve body, said surface recess circumferentially aligned with the smaller conduit of said valve body; and
a bar coupled to the main body of said valve stem, said bar circumferentially aligned with the exit port and opening of the distal section of said valve stem, whereby alignment of said surface recess with said bar indicates alignment of the exit port of said valve stem with the smaller conduit of said valve body.

18. The valve-stopcock combination of claim 17, wherein said surface recess and bar are colored.

* * * * *

UNITED STATES PATENT AND TRADEMARK OFFICE
CERTIFICATE OF CORRECTION

PATENT NO. : 5,178,186
DATED : January 12, 1993
INVENTOR(S) : Joseph E. Levasseur It is certified that error appears in the above-indentified patent and that said Letters Patent is hereby corrected as shown below:

| Column | Line | |
|--------|------|---|
| 6 | 28 | Change "claim 5" to --claim 3--. |
| 8 | 33 | After "body;" insert --and--. |

Signed and Sealed this

Twenty-third Day of November, 1993

BRUCE LEHMAN

Attest:

Attesting Officer

Commissioner of Patents and Trademarks